United States Patent
Yang et al.

(10) Patent No.: US 8,155,756 B2
(45) Date of Patent: Apr. 10, 2012

(54) MOTION-BASED OPTIMIZATION FOR PLACEMENT OF CARDIAC STIMULATION ELECTRODES

(75) Inventors: Michael Yang, Thousand Oaks, CA (US); Euljoon Park, Valencia, CA (US); Kyungmoo Ryu, Palmdale, CA (US); Stuart Rosenberg, Castaic, CA (US); Michael J. Coyle, Bell Canyon, CA (US)

(73) Assignee: Pacesetter, Inc., Sylmar, CA (US)

( * ) Notice: Subject to any disclaimer, the term of this patent is extended or adjusted under 35 U.S.C. 154(b) by 357 days.

(21) Appl. No.: 12/392,964

(22) Filed: Feb. 25, 2009

(65) Prior Publication Data
US 2009/0157136 A1 Jun. 18, 2009

Related U.S. Application Data

(63) Continuation-in-part of application No. 11/676,108, filed on Feb. 16, 2007.

(51) Int. Cl.
*A61N 1/00* (2006.01)
*A61B 5/05* (2006.01)
*A61B 5/02* (2006.01)

(52) U.S. Cl. ......... 607/116; 607/115; 600/424; 600/508
(58) Field of Classification Search .......... 607/115–116; 600/424, 508
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 5,297,549 A | 3/1994 | Beatty et al. | |
| 5,466,254 A | 11/1995 | Helland | |
| 5,476,483 A | 12/1995 | Bornzin et al. | |
| 5,553,611 A | 9/1996 | Budd et al. | |
| 6,240,307 B1 | 5/2001 | Beatty et al. | |
| 6,314,323 B1 | 11/2001 | Ekwall | |
| 6,501,983 B1 | 12/2002 | Natarajan et al. | |
| 6,885,889 B2 | 4/2005 | Chinchoy | |
| 6,947,785 B1 | 9/2005 | Beatty et al. | |
| 6,978,168 B2 | 12/2005 | Beatty et al. | |
| 7,613,500 B2 | 11/2009 | Vass et al. | |
| 2002/0188201 A1* | 12/2002 | Crowley | 600/439 |
| 2005/0149138 A1 | 7/2005 | Min et al. | |
| 2006/0161211 A1 | 7/2006 | Thompson et al. | |
| 2006/0167529 A1 | 7/2006 | Schecter | |

(Continued)

FOREIGN PATENT DOCUMENTS

WO 2006042039 A2 4/2006

(Continued)

OTHER PUBLICATIONS

Notice of Allowance, mailed Jun. 28, 2011—Related U.S. Appl. No. 12/416,771.

(Continued)

*Primary Examiner* — Nicole F Lavert

(57) ABSTRACT

An exemplary method includes use of a multielectrode device that can help position a cardiac stimulation lead to an optimal site in the heart based at least in part on cardiac motion information acquired via the multielectrode device and one or more pairs of current delivery electrodes that establish potential fields (e.g., for use as a coordinate system). An exemplary multielectrode device may be a multielectrode catheter or a multifilar, electrode-bearing guidewire. Various other exemplary methods, devices, systems, etc., are also disclosed.

19 Claims, 12 Drawing Sheets

U.S. PATENT DOCUMENTS

| | | |
|---|---|---|
| 2006/0178586 A1 | 8/2006 | Dobiak, III |
| 2006/0178589 A1 | 8/2006 | Dobiak, III |
| 2007/0135721 A1 | 6/2007 | Zdeblick |
| 2007/0167758 A1 | 7/2007 | Costello |
| 2007/0208260 A1* | 9/2007 | Afonso ............ 600/508 |
| 2008/0058656 A1 | 3/2008 | Costello et al. |
| 2008/0183072 A1 | 7/2008 | Robertson et al. |
| 2008/0242976 A1 | 10/2008 | Robertson et al. |
| 2009/0093857 A1 | 4/2009 | Markowitz et al. |

FOREIGN PATENT DOCUMENTS

| | | |
|---|---|---|
| WO | 2006105474 A2 | 10/2006 |
| WO | 2006105474 A3 | 10/2006 |
| WO | 2006042039 A3 | 7/2007 |
| WO | 2007120290 A2 | 10/2007 |
| WO | 2007120290 A3 | 10/2007 |

OTHER PUBLICATIONS

Gras, Daniel et al., "The selection of patients for cardiac resynchronization therapy," European Heart Journal Supplements (2004);Supplement D:D98-0100.

Kadish, Alan MD et al., "Mapping of Atrial Activation With a Noncontact, Multielectrode Catheter in Dogs," Circulation. 1999; 99:1906-1913.

Klemm, Hanno U. MD et al., "Simultaneous mapping of activation and motion timing in the healthy and chronically ischemic heart," Heart Rhythm 2006;3:781-788.

Paul, Thomas MD et al., "Atrial Reentrant Tachycardia After Surgery for Congenital Heart Disease. Endocardial Mapping and Radiofrequency Catheter Ablation Using a Novel, Noncontact Mapping System," Circulation. 2001;103:2266-2271.

* cited by examiner

MOTION-BASED OPTIMIZATION FOR PLACEMENT OF CARDIAC STIMULATION ELECTRODES

RELATED APPLICATIONS

This application is a continuation-in-part application of pending U.S. patent application Ser. No. 11/676,108, filed Feb. 16, 2007, entitled "Motion-based Optimization of Cardiac Stimulation Therapy," which is incorporated by reference herein.

TECHNICAL FIELD

Subject matter presented herein relates generally to cardiac pacing and/or stimulation therapy. Various examples concern mechanisms for optimizing such therapies based at least in part on cardiac motion.

BACKGROUND

Cardiac resynchronization therapy (CRT) aims to improve cardiac performance by synchronizing the ventricles. While the term "synchronization" is used, for some patients, a delay between contraction of the right ventricle and the left ventricle may be optimal. Hence, the term synchronization refers more generally to ventricular timing that improves cardiac performance. A general objective measure of lack of synchrony or dysynchrony is QRS width representative of contraction of both ventricles. For example, a QRS width greater than about 130 ms may indicate dysynchrony.

CRT can improve a variety of cardiac performance measures including left ventricular mechanical function, cardiac index, decreased pulmonary artery pressures, decrease in myocardial oxygen consumption, decrease in dynamic mitral regurgitation, increase in global ejection fraction, decrease in NYHA class, increased quality of life scores, increased distance covered during a 6-minute walk test, etc. Effects such as reverse modeling may also be seen, for example, three to six months after initiating CRT. Patients that show such improvements are classified as CRT "responders". However, for a variety of reasons, not all patients respond to CRT. For example, if a left ventricular stimulation lead cannot locate an electrode in a favorable position, then a patient may not respond to CRT.

Conventional placement criteria for a stimulation electrode typically focus on the location of latest electrical activation over the left ventricle. However, ischemic cardiomyopathy can cause non-uniform propagation of electrical activity over the myocardium. Thus, a site of latest electrical activation may not be optimal. In particular, such a site may be a poor candidate for maximizing cardiac stroke volume.

As described herein, various exemplary technologies aim to improve response to CRT. In particular, various techniques include use of cardiac motion information to determine an optimal stimulation site and/or to position an electrode at an optimal stimulation site.

SUMMARY

An exemplary method includes use of a multielectrode device that can help position a cardiac stimulation lead to an optimal site in the heart based at least in part on cardiac motion information acquired via the multielectrode device and one or more pairs of current delivery electrodes that establish potential fields (e.g., for use as a coordinate system). An exemplary multielectrode device may be a multielectrode catheter or a multifilar, electrode-bearing guidewire. Various other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, system, etc., aim to improve response to CRT and, particularly, to improve positioning of one or more electrodes to stimulate the heart. As described herein, various techniques acquire information about cardiac mechanics, e.g. contraction of a chamber of the heart. For example, an exemplary method includes positioning a plurality of electrodes in the heart and tracking motion of the electrodes during at least part of a cardiac cycle. Such electrodes may be associated with a catheter or a guidewire for temporary placement and configured to guide an electrode-bearing lead to an optimal site or sites. Motion tracking may be achieved in any of a variety of manners. For example, electrode patches may be placed on a patient's body to define a coordinate system (e.g., 1-D, 2-D, 3-D, etc.) and to aid in acquisition of motion information for one or more implanted electrodes (e.g., due to cardiac mechanics). An implanted electrode may be positioned via a vessel (e.g., a vein) such as the coronary sinus to acquire motion information about the left ventricle. An implanted electrode may be used to deliver stimulation energy from a particular stimulation site and where multiple electrodes are implanted, various stimulation sites may be tested. Motion information may be analyzed with respect to stimulation energy delivered using one or more stimulation sites to determine an optimal stimulation site or an optimal electrode configuration.

An exemplary approach may use a multielectrode catheter, a multifilar, electrode-bearing guidewire or a combination of both where the catheter or guidewire can help position a lead intended for chronic implantation. More generally, an exemplary multielectrode device allows for acquisition of cardiac motion information and for optimal placement of a lead (or one or more lead-based electrodes).

Exemplary Stimulation Device

The techniques described below are intended to be implemented in connection with any stimulation device that is configured or configurable to delivery cardiac therapy and/or sense information germane to cardiac therapy.

Figure 1:
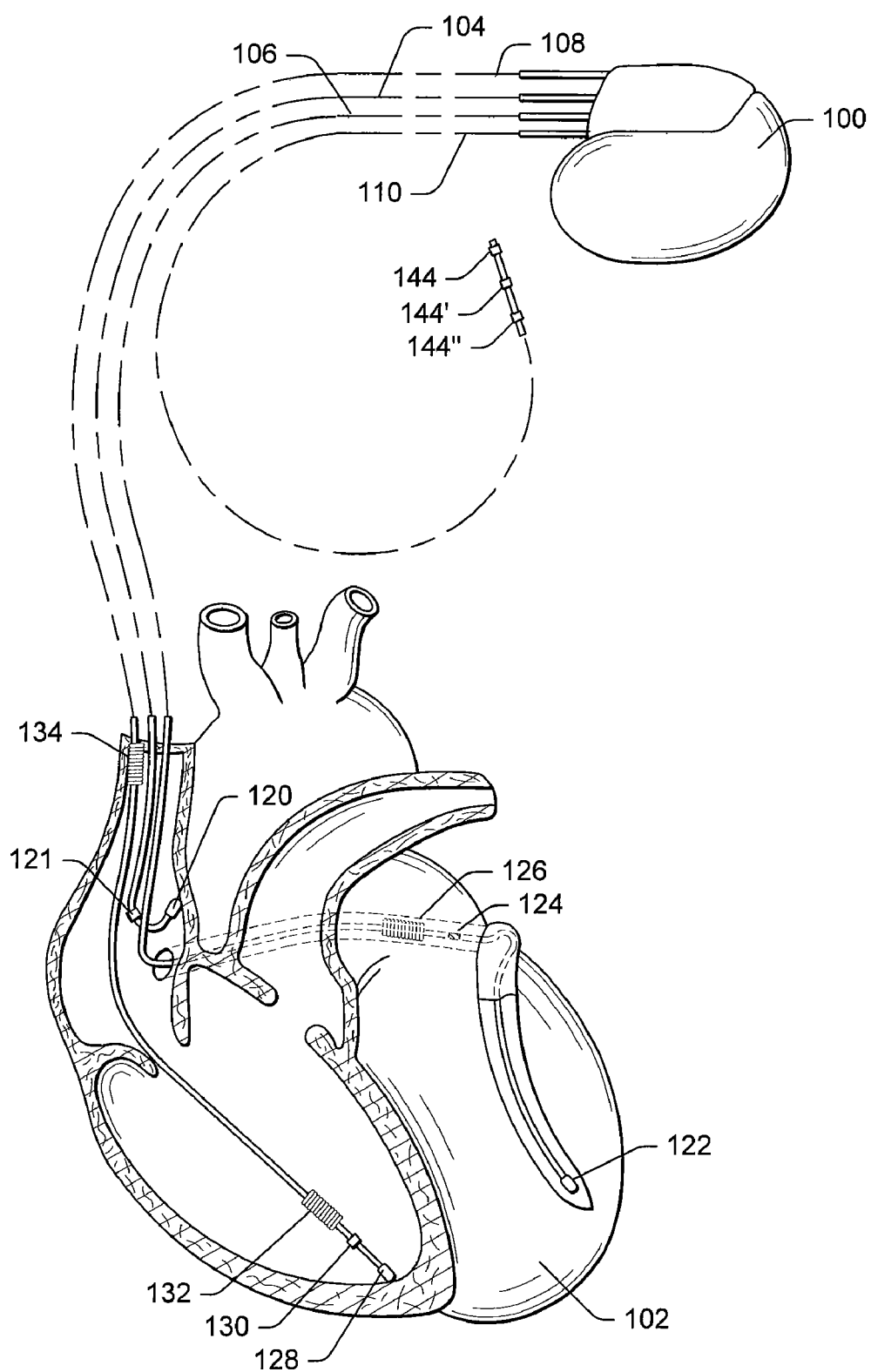
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of nerves or other tissue. Such a lead may include bifurcations or legs. For example, an exemplary coronary sinus lead includes pacing electrodes capable of delivering pacing pulses to a patient's left ventricle and at least one electrode capable of stimulating an autonomic nerve.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead.

Figure 2:
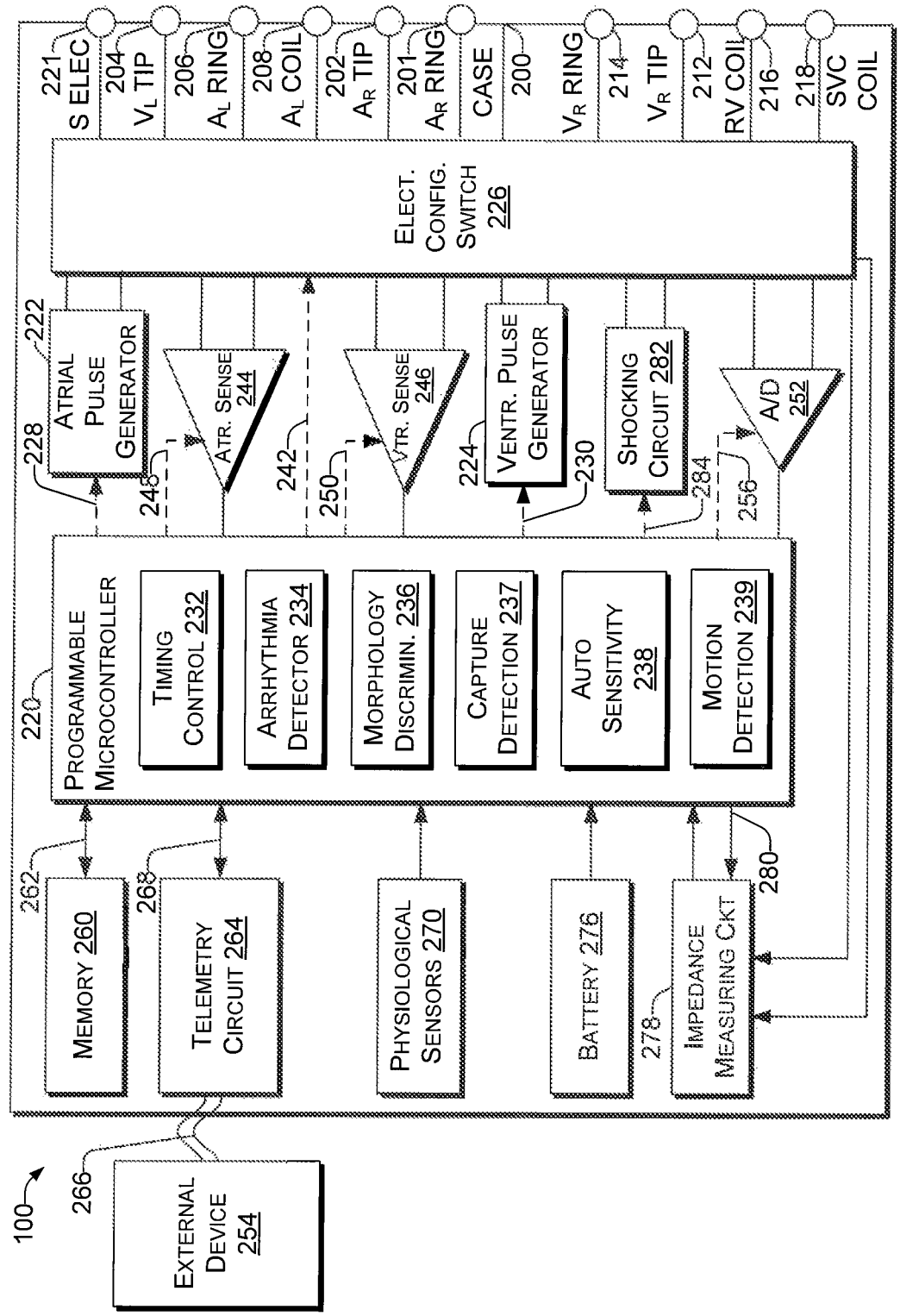
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional motion detection module 239. The module 239 may be used for purposes of acquiring motion information, for example, in conjunction with an external device that may use body surface patches or other electrodes. The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. In various examples, a measured potential corresponds to a position in a potential field and changes in position with respect to time represent motion. Such a module may help monitor cardiac mechanics in relationship to cardiac resynchronization therapy. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves" or "Fib-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Figure 11:
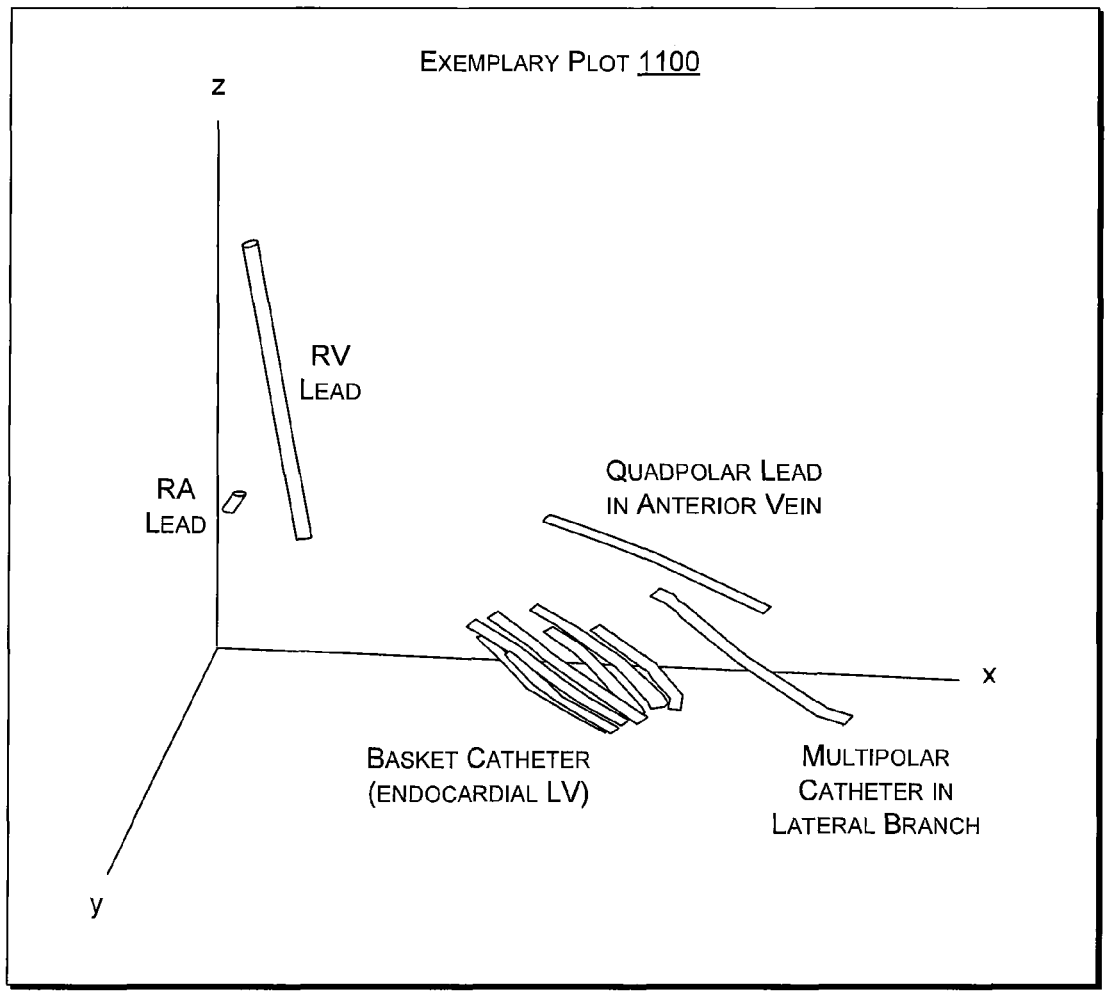
FIG. 11 is a plot of data acquired for trials in an animal model.

Cardiac signals are also applied to inputs of an analog-to-digital (A/D) data acquisition system 252. Additional configurations are shown in FIG. 11 and described further below. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, where the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, where an activity sensor is monitored diurnally to detect the low variance in the measurement corresponding to the sleep state. For a complete description of the activity variance sensor, the reader is directed to U.S. Pat. No.

5,476,483 (Bornzin et. al), issued Dec. 19, 1995, which patent is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Various exemplary methods, devices, systems, etc., may rely on resistance, resistivity, impedance and/or conductance for acquiring coordinates, locating electrodes and/or locating, directly or indirectly, one or more cardiac features, especially with respect to time. Resistance in an electric conductor is defined as the quotient of potential difference across the conductor and the current through the conductor. The resistance of a conductor is directly proportional to its length and inversely proportional to its cross-sectional area. A proportionality constant for resistance and length and resistance and cross-sectional area may be defined as the resistivity of the material of the conductor (resistivity typically has units of ohms-cm). Further, the reciprocal of the resistivity gives the conductivity of the material (siemens/cm). Resistivity is also the proportionality constant between the electric field and the current density and the inverse of conductivity. For many materials, resistivity depends on current frequency.

In instances where only a single frequency is used, the imaginary part may be deemed negligible or not relevant and the impedance may be approximated by the product of the reciprocal of an area over length scaling factor and the resistivity.

Conductance is the reciprocal of resistance in a direct current circuit, measured in siemens (formerly mhos) while in an alternating current circuit, conductance is the resistance divided by the square of impedance, also measured in siemens. Electrical impedance, typically symbolized by Z, is a complex number that has the same units (ohms) as resistivity and the ratio of voltage to current when these are represented by phasor quantities in alternating current circuits. Impedance is the total passive opposition offered to the flow of electric current and may be determined by the particular combination of resistance, inductive reactance, and capacitive reactance in a given circuit. Impedance is a function of frequency, except in the case of purely resistive networks.

As discussed herein, various exemplary techniques deliver current and measure potential where potential varies with respect to cardiac mechanics. For example, electrodes for delivery of current may be placed at locations that do not vary significantly with respect to cardiac mechanics while one or more electrodes for measuring potential may be placed at a location or locations that vary with respect to cardiac mechanics. Alternatively, electrodes for measuring potential may be placed at locations that do not vary significantly with respect to cardiac mechanics while one or more electrodes for delivery of current may be placed at a location or locations that vary with respect to cardiac mechanics. Various combinations of the foregoing arrangements are possible as well. Electrodes may be associated with a catheter or a lead. In some instances, an electrode may be a "stand-alone" electrode, such as a case electrode of an implantable device (see, e.g., the case electrode 200 of the device 100 of FIGS. 1 and 2).

With respect to the foregoing discussion of current delivery and potential measurement, a system such as the ENSITE® NavX system (St. Jude Medical, Inc.) can deliver low level separable currents from the three substantially orthogonal electrode pairs positioned on the body surface. The specific position of a catheter tip electrode within a chamber of the heart can then be established based on three resulting potentials measured between the recording tip electrode with respect to a reference electrode, as seen over the distance from each patch set to the recording tip electrode. Sequential positioning of a catheter at multiple sites along the endocardial surface of a specific chamber can establish that chamber's geometry, i.e., position mapping. The ENSITE® NavX system also permits the simultaneous display of multiple catheter electrode sites, and also reflects real-time motion of both ablation catheters and those positioned elsewhere in the heart.

Figure 3:
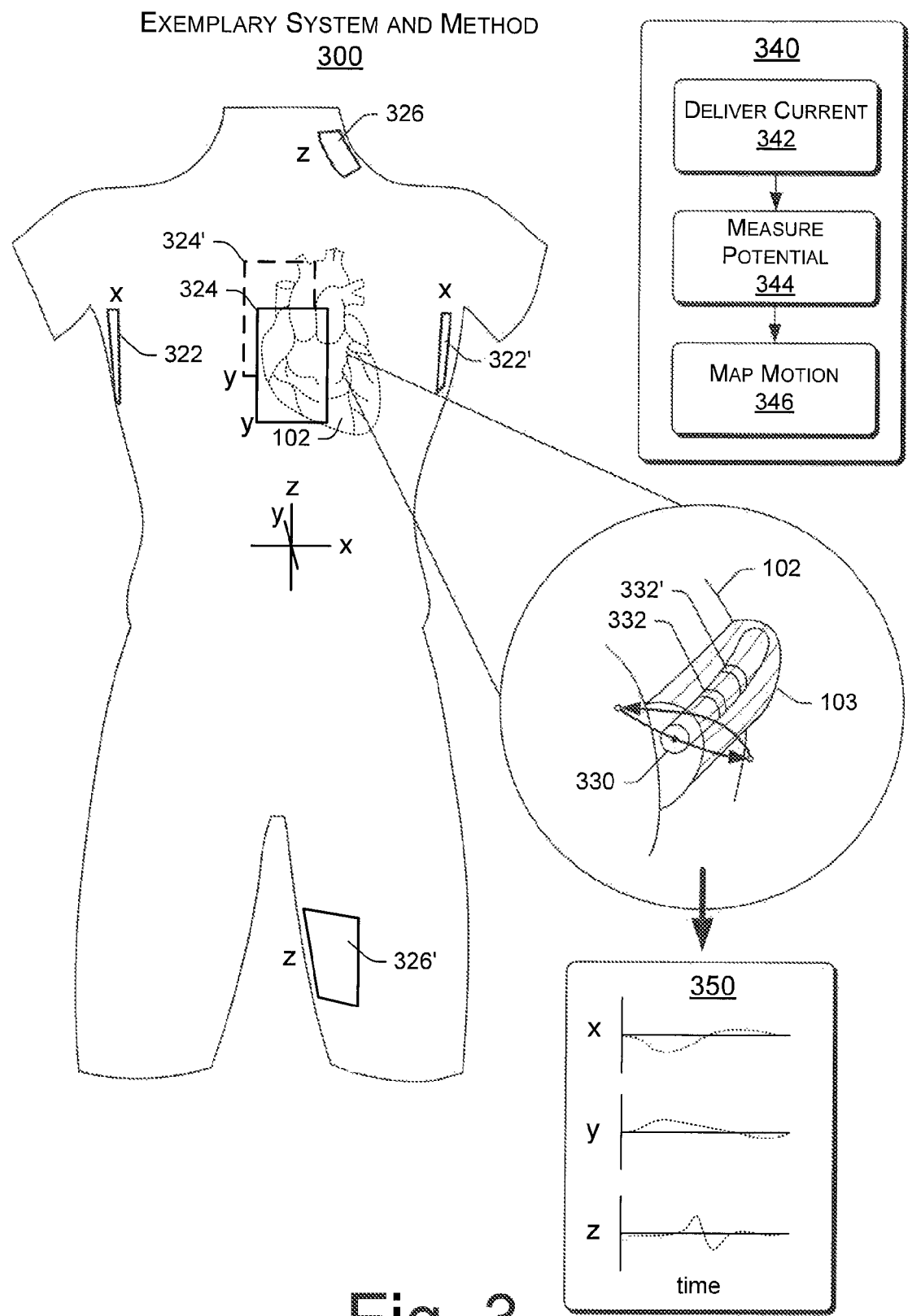
FIG. 3 is an exemplary arrangement of a lead and electrodes for measuring motion associated with cardiac activity.

FIG. 3 shows an exemplary system and method 300 for tracking motion of an electrode in one or more dimensions. For example, a plot 350 of position versus time for three dimensions corresponds to motion of one or more electrodes of a lead 330 positioned in a vessel 103 of the heart 102 where the lead 330 includes one or more electrodes 332, 332'. Two arrows indicate possible motion of the lead 330 where hysteresis may occur over a cardiac cycle. For example, a systolic path may differ from a diastolic path. An exemplary method may analyze hysteresis for any of a variety of purposes including selection of a stimulation site, selection of a sensing site, diagnosis of cardiac condition, etc.

An exemplary method 340 includes a delivery block 342 for delivery of current, a measurement block 344 to measure potential in a field defined by the delivered current and a mapping block 346 to map motion based at least in part on the measured potential. According to such a method, motion during systole and/or diastole may be used for selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc. As described herein, motion may be determined directly from potential or potential may indicate position where changes in position over time indicate motion. For example, motion may be based on a position acquired at one point in a cardiac cycle and another position acquired at another point in a cardiac cycle.

The system 300 may use one or more features of the aforementioned ENSITE® NavX system. For example, one or more pairs of electrodes (322, 322', 324, 324', 326, 326') may be used to define one or more dimensions (e.g., of a coordinate system) by delivering an electrical signal or signals to a body and/or by sensing an electrical signal or signals. Such electrodes (e.g., patch electrodes) may be used in conjunction with one or more electrodes positioned in the body (e.g., the electrodes 332, 332').

The exemplary system 300 may be used to track motion of one or more electrodes due to systolic motion, diastolic motion, respiratory motion, etc. Electrodes may be positioned along the endocardium and/or epicardium during a scouting or mapping process for use in identifying the optimal location of an electrode or electrodes for use in delivering CRT. For example, a location may be selected for optimal stimulation, for optimal sensing, or other purposes (e.g., anchoring ability, etc.).

With respect to stimulation, stimulation may be delivered to control cardiac mechanics (e.g., contraction of a chamber of the heart) and motion information may be acquired where the motion information is associated with the controlled cardiac mechanics. An exemplary selection process may identify the best stimulation site based on factors such as extent of motion, synchronicity of motion where motion may be classified as systolic motion or diastolic motion. In general, motion information corresponds to motion of an electrode or electrodes (e.g., endocardial electrodes, epicardial electrodes, etc.).

As described herein, a lead may be positioned using an electrode-bearing catheter or an electrode-bearing guidewire. Various examples refer to a multielectrode catheter or to a multifilar, electrode-bearing guidewire. Other arrangements are possible. More generally, various methods include positioning one or more electrodes within the heart and/or surrounding space (e.g., intra-chamber, intra-vascular, intrapericardial, etc., which may be collectively referred to as "cardiac space"). Access to the cardiac space may occur in any of a variety of manners (e.g., subxiphoid percutaneous puncture, transvenous perforation of a cardiac vein, tranmyocardial puncture via a transvenous approach, etc.). An exemplary multielectrode catheter may include a lumen configured to receive a lead while an exemplary lead may include a lumen that allows the lead to be guided by an exemplary multifilar, electrode-bearing guidewire.

A multielectrode catheter or a multifilar, electrode-bearing guidewire may be used in conjunction with the system and method of FIG. 3 where, for example, current is introduced using surface electrodes 322, 322', 324, 324', 326 and 326'.

Figure 4:
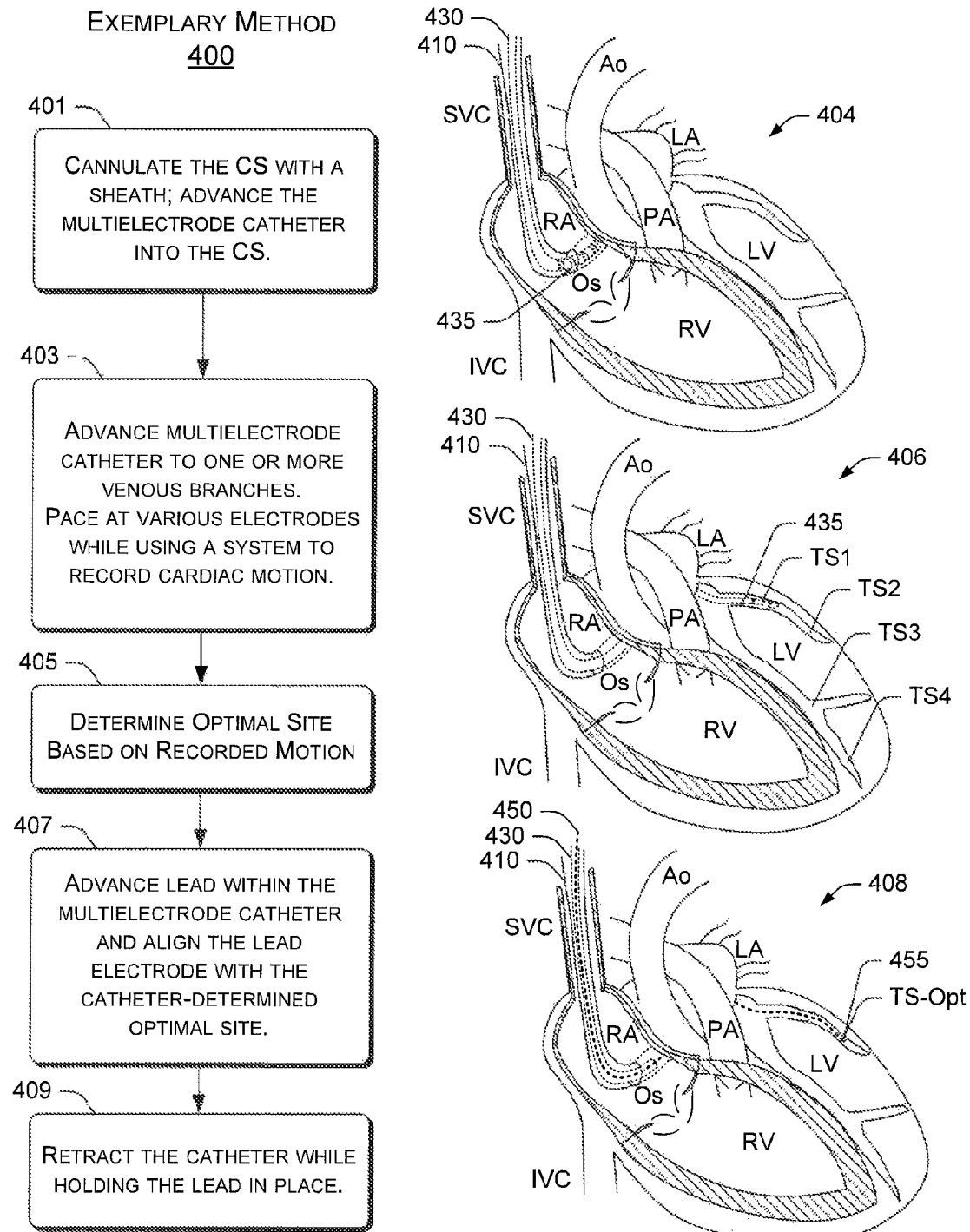
FIG. 4 is an exemplary method for positioning a lead for delivery of stimulation energy to the left ventricle.

FIG. 4 shows an exemplary method 400 for positioning a lead at an optimal site for electrical activation of the left ventricle. A series of diagrams 404, 406 and 408 illustrate how the method 400 may be performed. The method 400 commences in a cannulation block 401 where a clinician cannulates the coronary sinus with a sheath and advances a multielectrode catheter into the coronary sinus. The diagram 404 shows a sheath 410, positioned via the superior vena cava, and a multielectrode catheter 430, advanced via the sheath 410, where a series of electrodes 435 proximate to the distal end of the catheter 430 enter the coronary sinus via the ostium.

In an advancement block 403, the clinician advances the multielectrode catheter to one or more venous branches that feed the coronary sinus. At one or more of the branches, one or more electrodes of the multicatheter electrode may be used to pace the patient's heart and, in turn, a system such as the ENSITE® system may be used to record motion of the heart.

The diagram 406 shows electrodes 435 of the multicatheter electrode 430 positioned at a site TS1. Similarly, a clinician may position such electrodes 435 at various sites (e.g., TS2, TS3, TS4, etc.). At each site, individual electrodes may be used and corresponding motion recorded. Thus, a site may be located generally (e.g., based on a series of electrodes 435) or specifically (e.g., based on less than all of the electrodes 435).

In the example of FIG. 4, the method 400 continues in an optimization block 405. The optimization block 405, relies on recorded motion to determine an optimal site for delivery of stimulation energy to the left ventricle. For example, in the diagram 408, an optimal site TS-Opt is labeled.

Another advancement block 407 includes advancing an electrode-bearing lead within a lumen of the multielectrode catheter to align the lead (or one or more electrodes of the lead) with the catheter determined optimal site. The diagram 408 shows a lead 450 that includes one or more electrodes 455 as being advanced via a lumen of the catheter 430 to the optimal site TS-Opt.

In a retraction block 409, the method 400 continues with retraction of the multielectrode catheter while maintaining the position of the lead such that the lead (or one or more electrodes of the lead) remain at the identified optimal site. The diagram 408 shows the catheter 430 as being partially retracted to a position proximate the ostium of the coronary sinus while one or more electrodes of the lead 455 remain at the optimal site TS-Opt.

Figure 5:
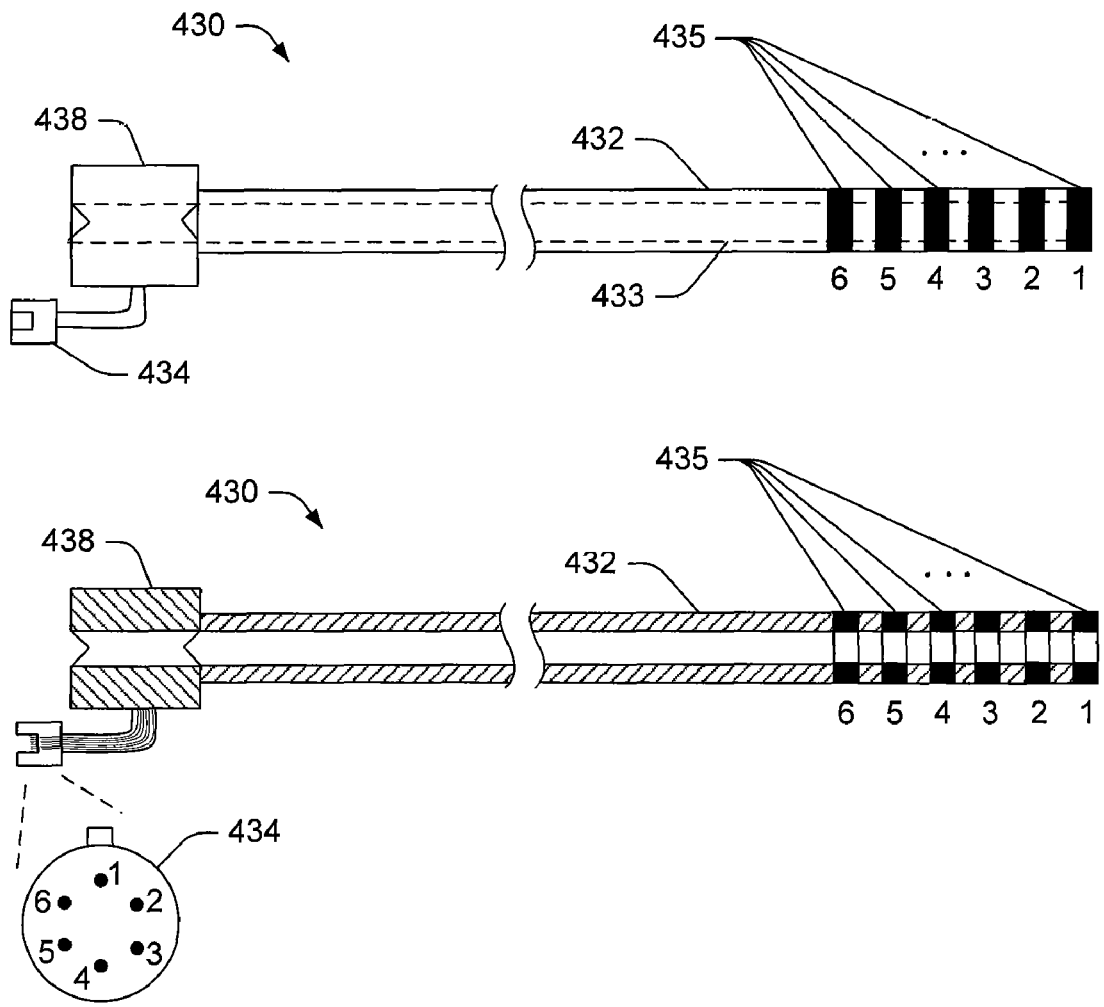
FIG. 5 is an exemplary arrangement of a multielectrode catheter suitable for measuring motion associated with cardiac activity that includes a lumen configured for advancing an electrode-bearing lead in a vein of the heart.

FIG. 5 shows a side view and a cross-sectional view of the exemplary multielectrode catheter 430 of the diagrams 404, 406, and 408 of FIG. 4. In this example, the catheter 430 includes a distal end and a proximate end and a substantially cylindrical wall 432 that defines a lumen 433. As described with respect to FIG. 4, a lead may be advanced via the lumen 433. The catheter 430 also includes a series of electrodes 435 are located at or near the distal end and a block 438 is located at the proximate end. A connector 434 allows for electrical connections to one or more of the series of electrodes 435. The electrodes 435 may be equally spaced, unevenly spaced, or a combination of evenly and unevenly spaced.

As described herein, an exemplary delivery tool is a catheter having multiple electrodes and a lumen for carrying a multi-electrode LV lead. Such a catheter may be placed in the coronary sinus to allow for access to veins of the left ventricle. An exemplary method can apply, on an electrode-by-electrode basis, stimulation energy to a patient's left ventricle and, in turn, motion of the delivery electrode, in response to the stimulation energy, can be mapped.

The foregoing method may be repeated for multiple electrodes or electrode configurations. Further, other parameters may be adjusted (e.g., energy, duration, polarity, etc.). Such variations may be referred to as motion trials. Acquired motion information for all or some of the motion trials may be mapped. Such mapping can be used to identify an optimal electrode site and configuration. An exemplary method may determine an optimal site based by identifying the electrode location that exhibited the greatest displacement in, for example, x, y and z directions.

As explained with respect to FIG. 4, prior to, during or after the mapping of catheter electrode motion, a left ventricular lead can be placed in the lumen of the catheter. Once the optimal electrode location is identified, the left ventricular lead can be positioned within the catheter, for example, to align one of its electrodes with the optimal catheter electrode. The catheter can then be withdrawn (e.g., retracted), leaving the left ventricular lead electrode at the optimal site.

If desired or needed, movement of the left ventricular lead during catheter withdrawal may be corrected. For example, a left ventricular lead may allow for use of a stylet for repositioning an electrode to a mapped site. Alternatively, a left ventricular lead may be extended so its electrodes are in a coronary vein beyond the distal end of the delivery catheter, thereby extending the length of track that is mapped for the performance measurement. After such additional mapping, the lead may be positioned at the optimal electrode site.

As described herein, a multielectrode catheter may be constructed of a straight or pre-curved polymer tube that has some compliance to allow it to negotiate the coronary venous system and respond to the motion of the heart. Electrodes of an exemplary catheter may be rings or ring segments about the circumference of the catheter, arranged axially along the distal portion of the catheter. As mentioned, with respect to electrode spacing, it may be desirable for the electrodes to have space between catheter electrodes equal to the space between like electrodes on a typical left ventricular lead, or some fraction thereof, in order to better approximate achievable pacing vectors.

Referring again to the catheter 430 of FIG. 5, conductor cables or wires can transmit signals between the electrodes and the proximal end of the catheter, where each one or more connectors can join the delivery catheter to an ENSITE® system or another mapping, recording, or stimulation device.

Figure 6:
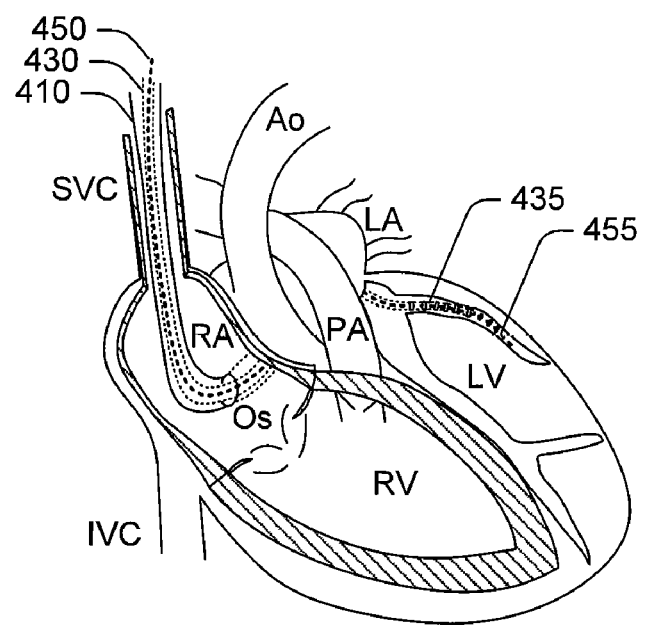
FIG. 6 is a perspective view of a portion of a system that includes a multielectrode catheter and an electrode-bearing lead positioned in a lumen of the multielectrode catheter.
Figure 6:
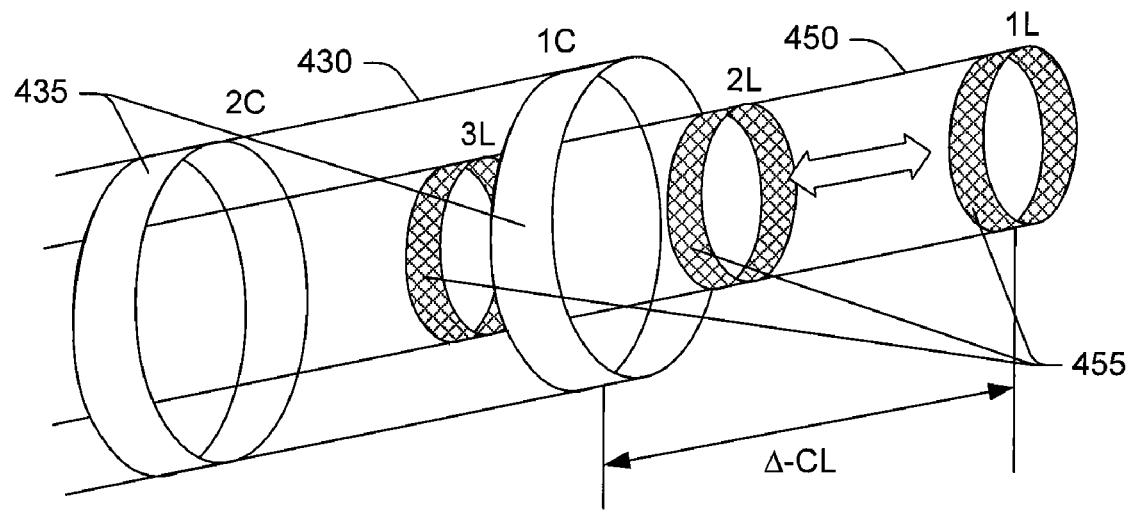

FIG. 6 shows a perspective view of a portion of a multielectrode catheter 430 and an electrode-bearing lead 450. As mentioned, to reach positions in narrow veins, an electrode-bearing lead may be extended beyond a distal end of a catheter. For example, in FIG. 6, the lead 450 is extended a distance Δ-CL beyond the distal end of the catheter 430. FIG. 6 also shows a diagram of the heart where the electrodes 455 of the lead 450 are positioned in a vein upstream the electrodes 435 of the catheter 430.

Figure 7:
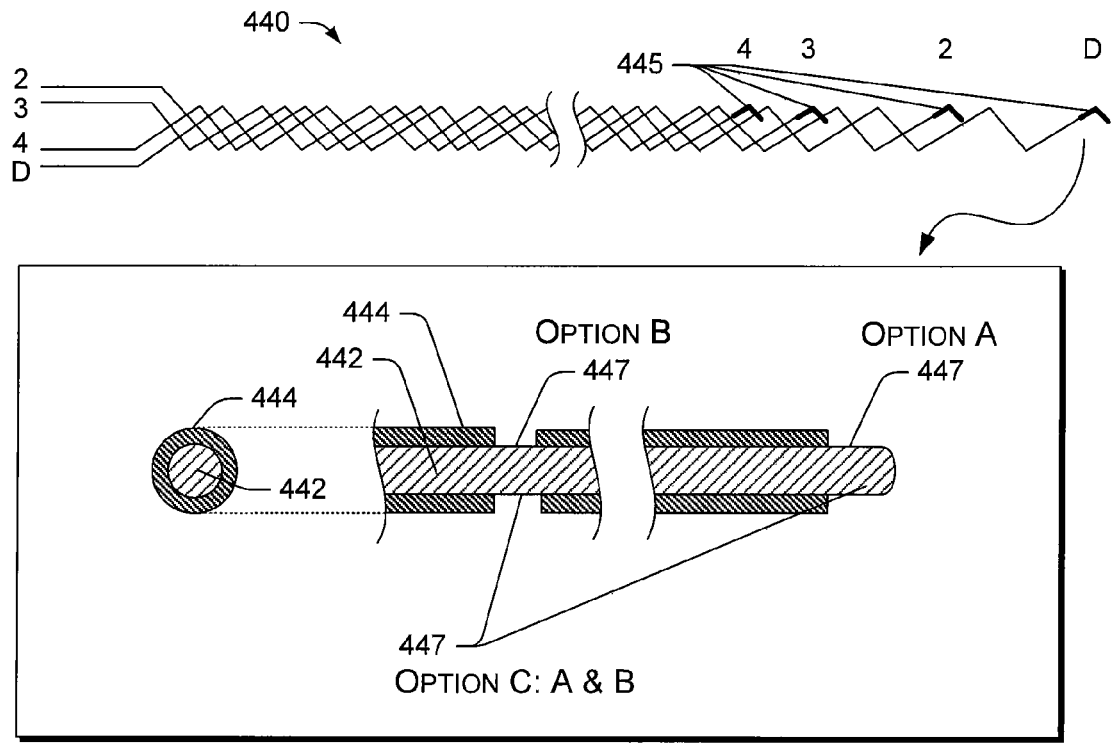
FIG. 7 is a diagram of several exemplary arrangements of a multifilar, electrode-bearing guidewire suitable for measuring motion associated with cardiac activity.
Figure 7:
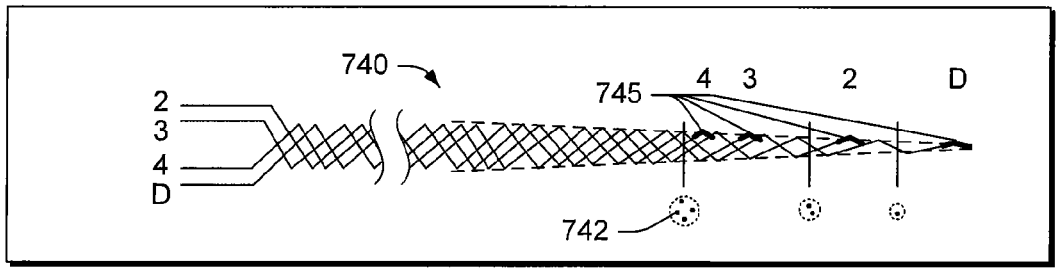
Figure 7:
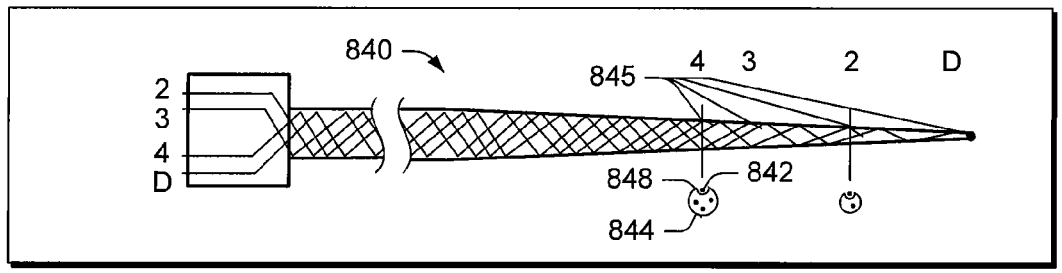

As mentioned, an exemplary system may include a multifilar, electrode-bearing guidewire to acquire motion information and to optionally guide a lead to a desired position in the heart of a patient (e.g., a vein receiving deoxygenated blood from myocardium of the left ventricle). FIG. 7 shows several exemplary arrangements for a guidewire 440, 740 and 840. In FIG. 7, the exemplary guidewires 440, 740 and 840 are shown as including multiple filars labeled D, 2, 3 and 4. Each of the filars includes an associated electrode portion, which form a series of electrodes 445, 745, 845. An electrode portion of a filar may include one or more electrodes. For example, a cross-sectional view of a filar of the guidewire 440 shows a conductive core 442 surrounded by an insulator 444 where gaps in the insulation expose the core 442 to create one or more electrode surfaces 447.

The guidewires 440, 740 and 840 may vary in flexibility or resiliency. For example, for the guidewires 440, 740 and 840, the filar D extends beyond the filars 2, 3 and 4. Hence, the resiliency of the guidewires 440, 740 and 840 can vary from the distal end toward the proximal end as the number of filars increases from 1 to 4. Such an arrangement allows a guidewire to more readily access and navigate smaller veins at the distal end.

As described herein, a delivery tool can be a multielectrode guidewire such as one of the multifilar, electrode-bearing guidewires 440, 740 or 840 of FIG. 7. In an exemplary method, such a guidewire can be extended into a branch of the coronary venous system and its electrodes to track motion and/or pace the heart. Once an optimal electrode location is identified, a lead can be positioned over the guidewire to align one or more of its electrodes with one or more of the optimal guidewire electrodes. In turn, the guidewire can be withdrawn, leaving the lead at an optimal site.

In an alternative approach, a lead may be deployed partway down the length of a guidewire during a mapping procedure such that the electrodes on both the guidewire and the lead are able to be paced and/or motion-tracked. Further, a plurality of such guidewires may be deployed through multiple branches in order to quickly gain more global information about motion. Such information can be used to electrically map the heart. Once mapped, a lead can be advanced along a guidewire that corresponds to a global optimal site.

As shown in FIG. 7, the guidewires 440, 740 and 840 are multifilar, that is, constructed of more than one independent wire, for example, coiled co-helically about a common axis. The wires can be made of a conductor core such as stainless steel, platinum or other metal alloys (e.g., MP35N alloy, which is a nonmagnetic, nickel-cobalt-chromium-molybdenum alloy possessing a unique combination of ultrahigh tensile strength (up to 300 ksi [2068 MPa]). In the guidewires 440 and 740 of FIG. 7, each filar is an individual wire that is coated with an insulating polymer such as ePTFE. The coating is removed from a small portion or portions of each filar at and/or near the distal end of the guidewire, exposing a conductive core and creating an electrode. The exposed portion can be staggered from one wire to the next, creating a linear array of electrodes. A coating can be mechanically removed, removed via a laser technique, chemically removed, or other suitable technique. Alternatively, during the coating process a mask can be placed to prevent coating of the regions designated to be the linear array of electrodes.

A conductor can be exposed while leaving insulation both proximal and distal to an exposed portion, or a conductor can be exposed at the distal end of the filar, staggering the overall length of each filar with respect to the others.

As mentioned, a staggered configuration of filars can provide an advantage of the tip of the mapping guidewire being floppier than the main portion of the guidewire, which may act to reduce risk of perforation of the guidewire through the wall of a vein (e.g., coronary vein associated with the left ventricle). At the proximal end of the guidewire, each filar can connect to an ENSITE® system or another mapping, recording, or stimulation device.

For the guidewires 740 and 840 of FIG. 7, the diameter or effective diameter of the guidewire is shown as decreasing over at least a portion of the length from the proximal end to the distal end. Cross-sectional views of the guidewire 740 show individual filars (e.g., filar 742) that provide for an effective diameter while cross-sectional views of the guidewire 840 show individual filars in a body 844 where a cutout or removed portion of the body 848 exposes a filar (e.g., the filar 842). In another example, a filar may simply extend slightly outside a body such that removal of material from the body 844 is not required. The body 844 of the guidewire 840 may be constructed from an electrically insulating material (i.e., an insulator). While the filars are shown as having a particular shape in the guidewire 840, other shapes may be used as the body 844 can provide support and allow for positioning of filars (and optionally insulating one filar from another).

In another example, the filars may be individually insulated yet set in a body with a decreasing diameter or other tapering shape that allows for navigation of a the multifilar guidewire into narrower veins. In general, such an arrangement will have a flexibility (e.g., floppiness) that is related to cross-sectional area, where a smaller cross-sectional area corresponds to increased flexibility (whether due to cross-sectional area of the body, the number of filars or a combination of the cross-sectional area of the body and the number of filars).

Figure 8:
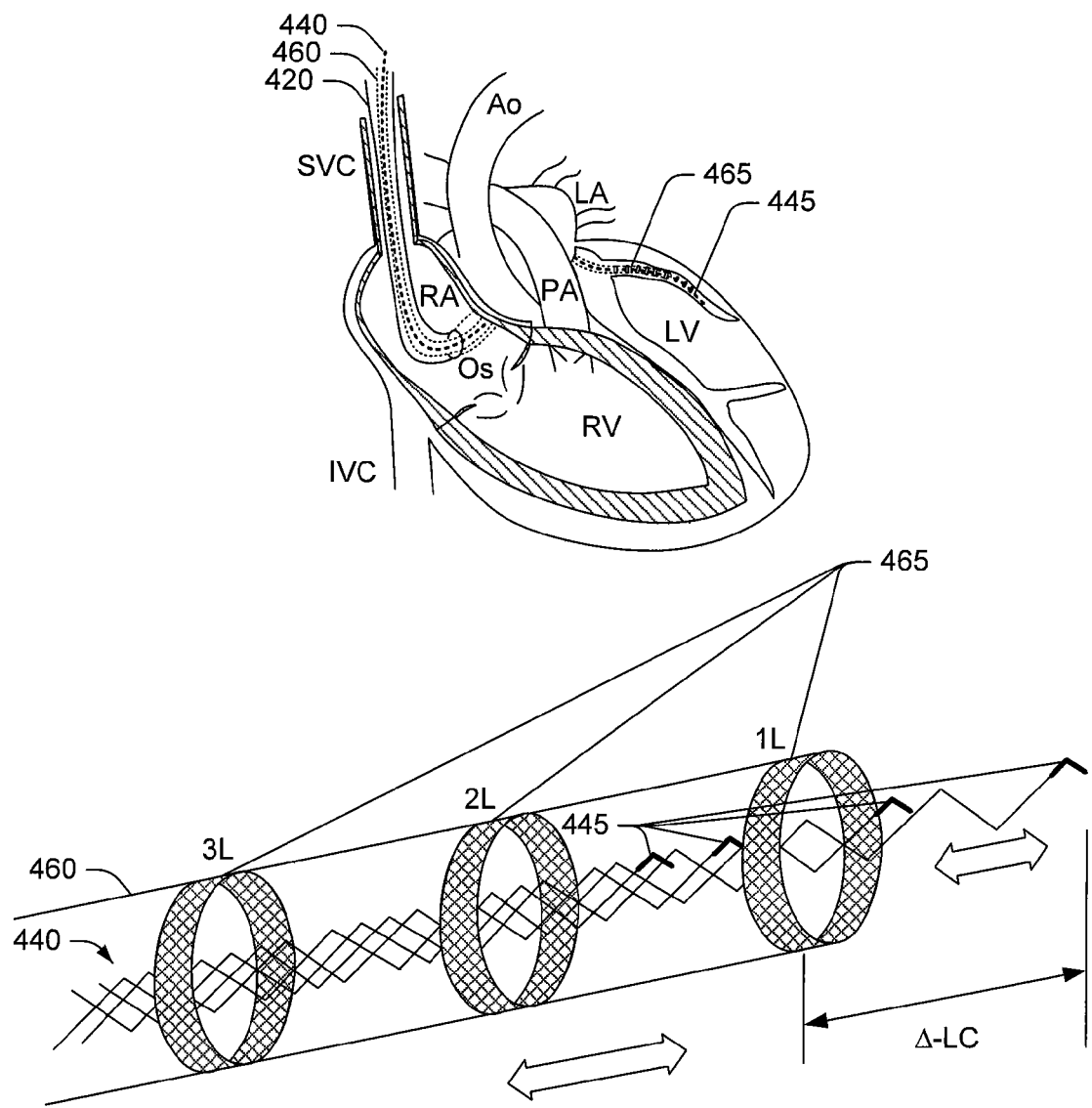
FIG. 8 is a perspective view of a portion of a system that includes a multifilar, electrode-bearing guidewire positioned in a lumen of an electrode-bearing lead.

FIG. 8 shows an exemplary arrangement of the multifilar guidewire 440 of FIG. 7. In the example of FIG. 8, a lead 460 can be positioned with respect to the guidewire 440 to establish a location or relationship for a series of lead electrodes 465 and a series of guidewire electrodes 445. An exemplary method can use the guidewire 440 to guide the lead 460 to a desired location. As indicated by arrows, the guidewire 440 can move independently of the lead 460 and vice versa. Such versatility in movement can allow for acquisition of motion information by the guidewire 440 and/or the lead 460. A diagram of the heart shows the series of electrodes 445 of the guidewire 440 as extending beyond the distal end of the lead 460 to reach an upstream venous position. Such a location may be used for motion trials even where a lead may be not capable of placement in the location.

Figure 9:
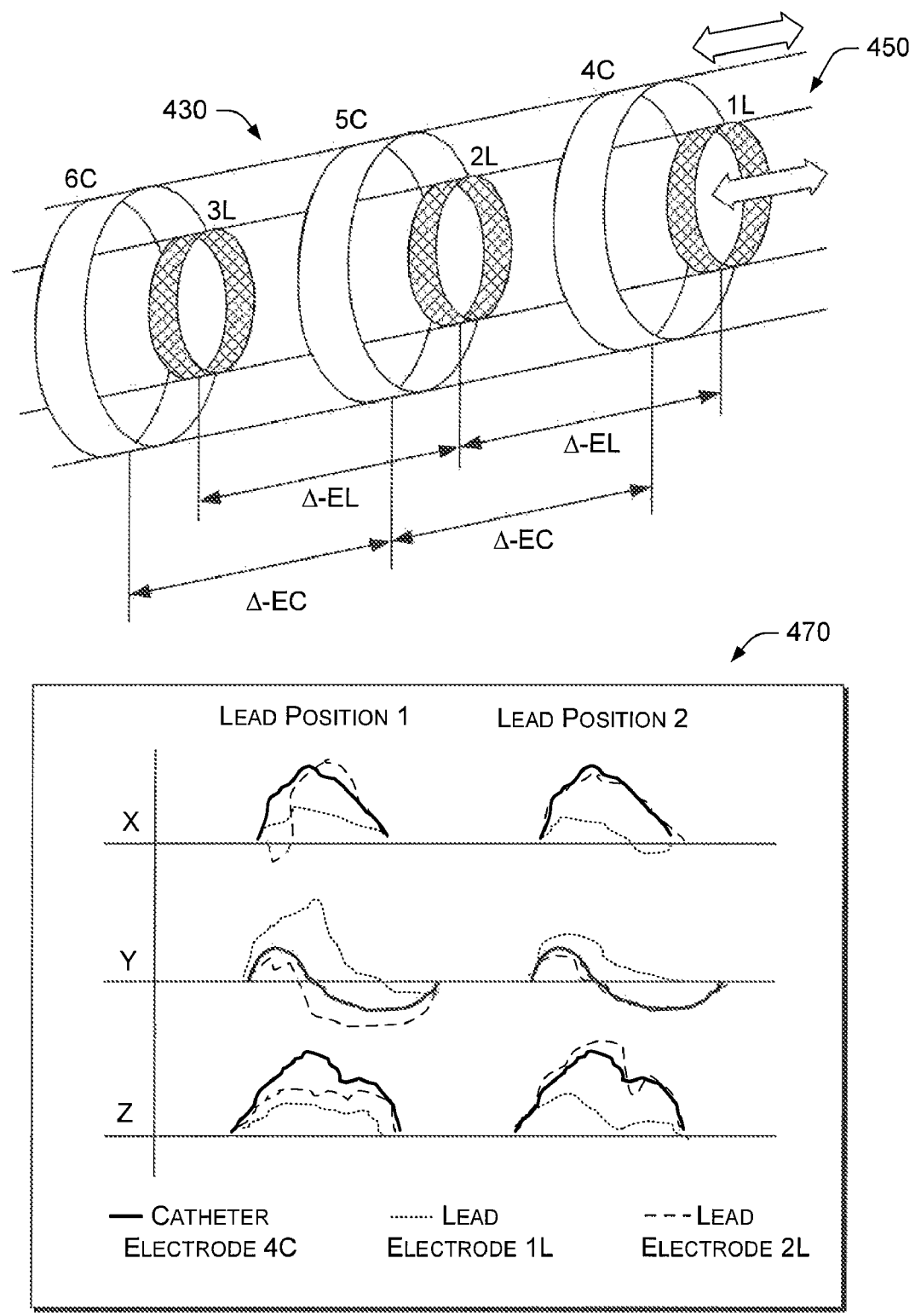
FIG. 9 is a perspective view of a portion of a system where electrodes of one component may be tracked with respect to electrodes of another component of the system.

FIG. 9 shows a diagram and series of plots that demonstrate how movement of catheter electrodes and lead electrodes may be tracked. Such tracking may be used to more accurately position one or more lead electrodes in an optimal location. In the example of FIG. 9, electrodes 4C and 5C and 5C and 6C of the catheter 430 are evenly spaced at a distance $\Delta$-EC. Similarly, electrodes 1L and 2L and 2L and 3L of the lead 450 are evenly spaced at a distance $\Delta$-EL. Known spacing may be used to facilitate tracking. For example, a series of plots 470 for electrode 4C of the catheter 430 and electrodes 1L and 2L of the lead 450 show how tracking may occur. Such a technique may be particularly useful where spacing between electrodes is large and where radiographic techniques are not readily available or contraindicated.

An exemplary method positions a lead electrode at a location deemed "optimal" or "desirable" using a catheter. In a Cartesian coordinate system, the method tracks each coordinate (x, y, z) of one or more catheter electrodes. For example, in the example 450 of FIG. 9, the method can track one or more of the catheter electrodes 4C, 5C, 6C (or others).

Such an exemplary method is further described with respect to the plot 470 of FIG. 9, which shows information in three dimensions (x, y, z) for catheter electrode 4C, lead electrode 1L and lead electrode 2L. Specifically, one set of dimensional information corresponds to a first lead position (Lead Position 1) and another set of dimensional information corresponds to a second lead position (Lead Position 2).

According to the method, where a catheter electrode 4C is the "optimal" location (e.g., as determined by any of a variety of techniques), a locating system such as the ENSITE® NavX system can record and display each coordinate of 4C throughout a cardiac cycle. With the catheter electrode 4C at the selected location, a clinician adjusts a lead, for example, by advancing the lead through the catheter. With a locating system (e.g., the ENSITE® NavX system), realtime position in each of (x,y,z) coordinates for all electrodes on the lead can be displayed or otherwise indicated (e.g., sound emission via a speaker) to the clinician or other care provider assisting in the locating procedure.

To determine a "correct" position for a lead electrode, the method can rely on degree of overlap of coordinate traces for the lead electrode and the catheter electrode (see, e.g., the plot 470 for x, y, z traces of the lead electrode 2L with respect to catheter electrode 4C and compare position 1 and position 2). In this approach, when the coordinate traces have the greatest degree of overlap, the lead electrode is in the "correct" position.

A locating system can include an algorithm that determines degree of overlap, for example, based on a difference between a trace for one electrode and another electrode (see, e.g., difference between trace of 2L and 4C in lead position 2 less than difference in lead position 1 for coordinates x, y and z).

In this example, the trace may be selected based on an entire cardiac cycle, a number of cardiac cycles (e.g., average trace), a portion of a cardiac cycle, etc. Depending on the use of the electrode, a portion of a cardiac cycle may be selected and correspond to a time period when the electrode senses cardiac activity or delivers energy to the patient's heart.

In some instances, an algorithm may rely on information from more than two electrodes to determine whether one or more electrodes are in desired locations. For example, where the spacing between two lead electrodes and two catheter electrodes is the same then to improve accuracy the algorithm can calculate differences for a first lead/catheter pair and a second lead/catheter pair.

As described herein, noting that the heart does not move uniformly over its surface or interior, dynamic position information can be used to determine if one electrode is at approximately the same location as another electrode. Further, such a technique can be used to determine that two electrodes are not at approximately the same location.

While the technique has been explained with respect to a catheter and a lead in a lumen of the catheter, such an approach can be taken for other arrangements (e.g., even where the electrodes have no structural relations that would cause one to move responsive to the other). For example, an electrode positioned in a surface vein of the heart and an epicardial electrode may be located to coincide based on an analysis of trace information in one or more dimensions where the trace information reflects cardiac motion (e.g., over at least a portion of a cardiac cycle).

As described herein, an exemplary algorithm performs a mathematical optimization to minimize residuals between a lead electrode position and a catheter electrode position. In such an example, realtime numeric feedback (value of residual) as well as graphical feedback (concordance of x, y, z traces) may be provided to a clinician. As an alternative to residuals by least squares fitting, area-under-curve, or computation of cross-correlation may be used between the catheter and lead electrode traces, in an effort to minimize a parameter.

In another alternative approach, an average position ($x_{ave}$, $y_{ave}$, $z_{ave}$) of a catheter electrode at its optimal location can be determined as the mean value of each coordinate throughout one or more cardiac cycles. The realtime moving-average position of each lead electrode can be tracked over the same time frame, and when the lead electrode average position coincides with or is nearest to the catheter electrode optimal average position, the lead can be appropriately positioned. In yet another alternative, position at a fiducial time point such as end-systole or end-diastole is used rather than the average position.

Various methods can be applied using the MFGW electrodes (e.g., instead of the MEC electrodes) to determine the optimal location in a manner where the lead electrode position is matched to the position of an optimal electrode.

An exemplary method for positioning a lead once an optimal electrode location has been determined (e.g., by an electrode on a catheter) includes advancing the lead until only its distal electrode protrudes beyond a distal end of a catheter (e.g., a sheath).

In such a method, as the distal electrode extends beyond the sheath, the motion signal for the distal electrode exhibits a sudden apparent shift (much larger in the ENSITE® NavX location system display than would be expected based on the physical amount of movement of the lead). By advancing the lead slowly through an introducer (e.g., catheter), one would expect to see a slow advancement on the ENSITE® NavX system display; however, at the point which the distal lead electrode first exits the guide catheter, a large/fast apparent movement is displayed due to the sudden change in the impedance field without the catheter material shielding the lead electrodes. The physical distance from the catheter tip to the optimal electrode, as previously determined, can be known. For example, if a catheter electrode spacing is $\Delta EC$ and the 4th electrode is at the optimal location, then the distance from catheter tip to optimal location is $4\Delta EC$. Since it is known that the lead tip is at the distal end of the catheter, the lead can be withdrawn the known distance (for example $4\Delta EC$), at which point the lead tip electrode (distal electrode) is located at the optimal location.

In an alternative approach, for a multielectrode lead, the amount the lead is advanced or withdrawn (e.g., retracted) can be computed by the difference between the distance from catheter tip to catheter electrode situated at the optimal location and the distance between lead distal electrode and another (more proximal) lead electrode to be situated at the optimal location.

An exemplary method includes positioning a lead over a multielectrode guidewire where one of the guidewire electrodes is situated at an optimal position. In this method, as the lead is advanced such that the tip electrode coincides with more proximal electrodes on the guidewire, the guidewire electrodes coincident with the lead body will show an apparent shift on locating system (e.g., the ENSITE® NavX system). The shift is due to changing impedance as the lead body masks the guidewire electrode. The lead is advanced until the optimal guidewire electrode first shows this shift in position, indicating that the lead tip is just covering the optimal guidewire electrode. With a multielectrode lead of known electrode spacing, the lead may be optionally advanced further by a known distance such that a proximal electrode on the lead coincides with the optimal location determined by the guidewire.

Many consider optimal hemodynamic support, accessibility of the desired vein location and adequate pacing parameters without phrenic nerve stimulation as three of the most important aspects for successful left ventricular lead implantation. In many cases, a lateral or posterior vein is the desired location for achieving optimal hemodynamic support as this is usually the site of most delayed activation of the left ventricular wall in patients with left bundle branch block.

Often lead placement is achieved via a stylet-guided lead or via intubation of the coronary sinus with a dedicated guiding catheter that provides support for advancing a lead or leads. For placement of a lead through a guiding catheter, techniques include a stylet-guided lead approach or an "over-the-wire" approach.

In an over-the-wire approach, a guidewire is advanced into a desired branch of the coronary sinus and a lead is then pushed over-the-wire, as guided by the wire. The over-the-wire approach is often suitable for placement of a lead in small tortuous veins. Fixation of a lead, once placed, may be achieved by small anchors at the tip, pre-shaped curves, helical screws, etc.

A target vein for left ventricular pacing is normally a left ventricular vein which empties into the coronary sinus. One or more sharp angles may exist between a target vein and the coronary sinus. Often such angles can be passed by placing an angiography catheter with a narrow curve (e.g. a right Judkins catheter or an internal mammary artery catheter) through the guiding catheter and directly intubating the coronary sinus side branch. In such a procedure, a guidewire can be placed in the distal part of the vein through the angiography catheter and the catheter withdrawn while keeping the guidewire in place. The pacing lead can then be advanced into the final location. Traditionally, angiography involves injecting a radio-opaque contrast agent into a blood vessel and imaging using X-ray based techniques such as fluoroscopy. Various exemplary techniques described herein can be performed without X-ray based techniques such as fluoroscopy.

Figure 10:
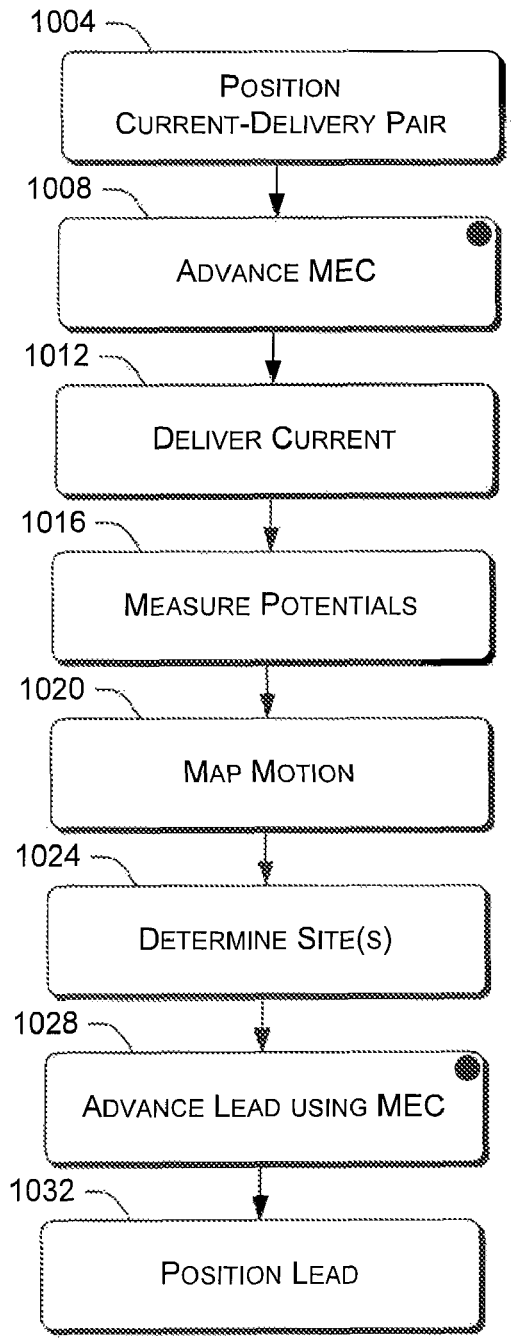
FIG. 10 is a block diagram of two exemplary methods.
Figure 10:
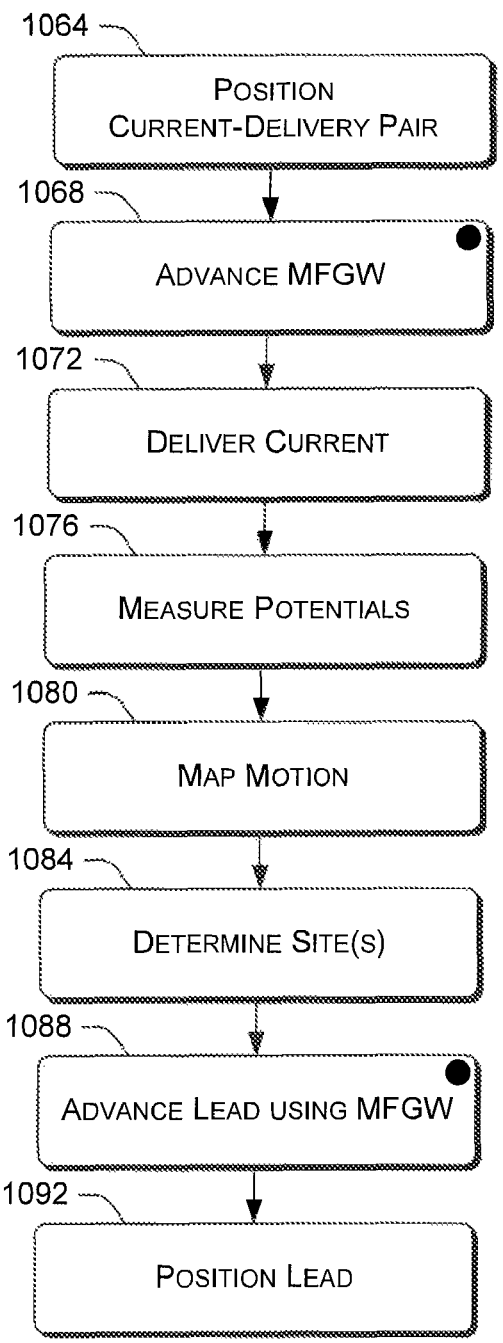

FIG. 10 shows two exemplary methods 1000 and 1060. The method 1000 relies on a multielectrode catheter (MEC) while the method 1060 relies on a multifilar, electrode-bearing guidewire (MFGW).

The method 1000 includes a positioning block 1004 to position a pair of current-delivery electrodes in contact with a patient's body. An advancement block 1008 advances a multielectrode catheter (MEC) into the coronary sinus of the patient's heart and at least partially into a vein of the left ventricle. A delivery block 1012 delivers current using the pair of current-delivery electrodes to generate a potential field. A measurement block 1016 measures potentials associated with the potential field using at least one electrode of the multielectrode catheter (MEC). A mapping block 1020 maps motion of the multielectrode catheter (MEC) based on the measured potentials. A determination block 1024 determines a site (or sites) for delivery of stimulation energy to stimulate the patient's heart based at least in part on the mapping. Another advancement block 1028 advances an electrode-bearing lead into a lumen of the multielectrode catheter (MEC). A positioning block 1032 positions the electrode-bearing lead based at least in part on the determined site(s).

The method 1060 includes a positioning block 1064 to position a pair of current-delivery electrodes in contact with a patient's body. An advancement block 1068 advances a multifilar, electrode-bearing guidewire (MFGW) into the coronary sinus of the patient's heart and at least partially into a vein of the left ventricle. A delivery block 1072 delivers current using the pair of current-delivery electrodes to generate a potential field. A measurement block 1076 measures potentials associated with the potential field using at least one electrode of the multifilar, electrode-bearing guidewire (MFGW). A mapping block 1080 maps motion of the multifilar, electrode-bearing guidewire (MFGW) based on the measured potentials. A determination block 1084 determines a site (or sites) for delivery of stimulation energy to stimulate the patient's heart based at least in part on the mapping. Another advancement block 1088 advances an electrode-bearing lead along the multifilar, electrode-bearing guidewire (MFGW). A positioning block 1092 positions the electrode-bearing lead based at least in part on the determined site(s).

The methods 1000 and 1060 both include use of a multielectrode device that can help position a cardiac stimulation lead to an optimal site in the heart based at least in part on cardiac motion information acquired via the multielectrode device and one or more pairs of current delivery electrodes that establish potential fields (e.g., for use as a coordinate system).

An exemplary method may include aspects of both the method 1000 and the method 1060. For example, an exemplary method may include use of a multielectrode catheter and a multifilar, electrode-bearing guidewire. Such a method may be defined, in part, on diameter where the catheter has the largest diameter, the guidewire has the smallest diameter and a lead has a diameter less than the largest diameter and greater than the smallest diameter. The use of two guiding mechanisms can help ensure that a lead is properly positioned.

As described herein, an exemplary method may include use of an outer cannulator and an inner cannulator or subselector, either or both of which may be fitted with electrodes. For example, a method may include cannulation of the coronary sinus by a first multielectrode catheter (MEC1), advancing a smaller second multielectrode catheter (MEC2) from within the first multielectrode catheter (MEC1), and advancing a lead and/or guidewire such as a multifilar, electrode-bearing guidewire (MFGW).

Motion information may be influenced by respiration. For example, respiratory sinus arrhythmia (RSA) causes an increase in heart rate during inspiration due to inhibition of parasympathetic nerve transmission and/or firing, which shifts autonomic tone or balance toward parasympathetic. While during expiration, heart rate decreases as parasympathetic nerve transmission and/or firing resumes. Motion information may also be affected by motion due to respiration. For example, intrathoracic pressure varies between inspiration and expiration, which can affect pericardial pressure. In turn, changes in pericardial pressure can affect motion of the myocardium. In addition, the thoracic cavity expands and contracts during respiration, which can cause the heart to shift position. Hence, respiration can alter motion information via cardiopulmonary effects, autonomic effects, pressure effects, position effects, etc.

To account for respiration, motion information can be acquired for a cardiac cycle that corresponds to, for example, peak inspiration or peak expiration. Such a gating technique acts to eliminate variation due to the effects of respiration. Where desired, such a method may acquire cardiac motion information for a cardiac cycle at or near peak inspiration and at a cardiac cycle at or near peak expiration. A comparison between cardiac motion information for these two states may provide insight into cardiac mechanics.

Figure 12:
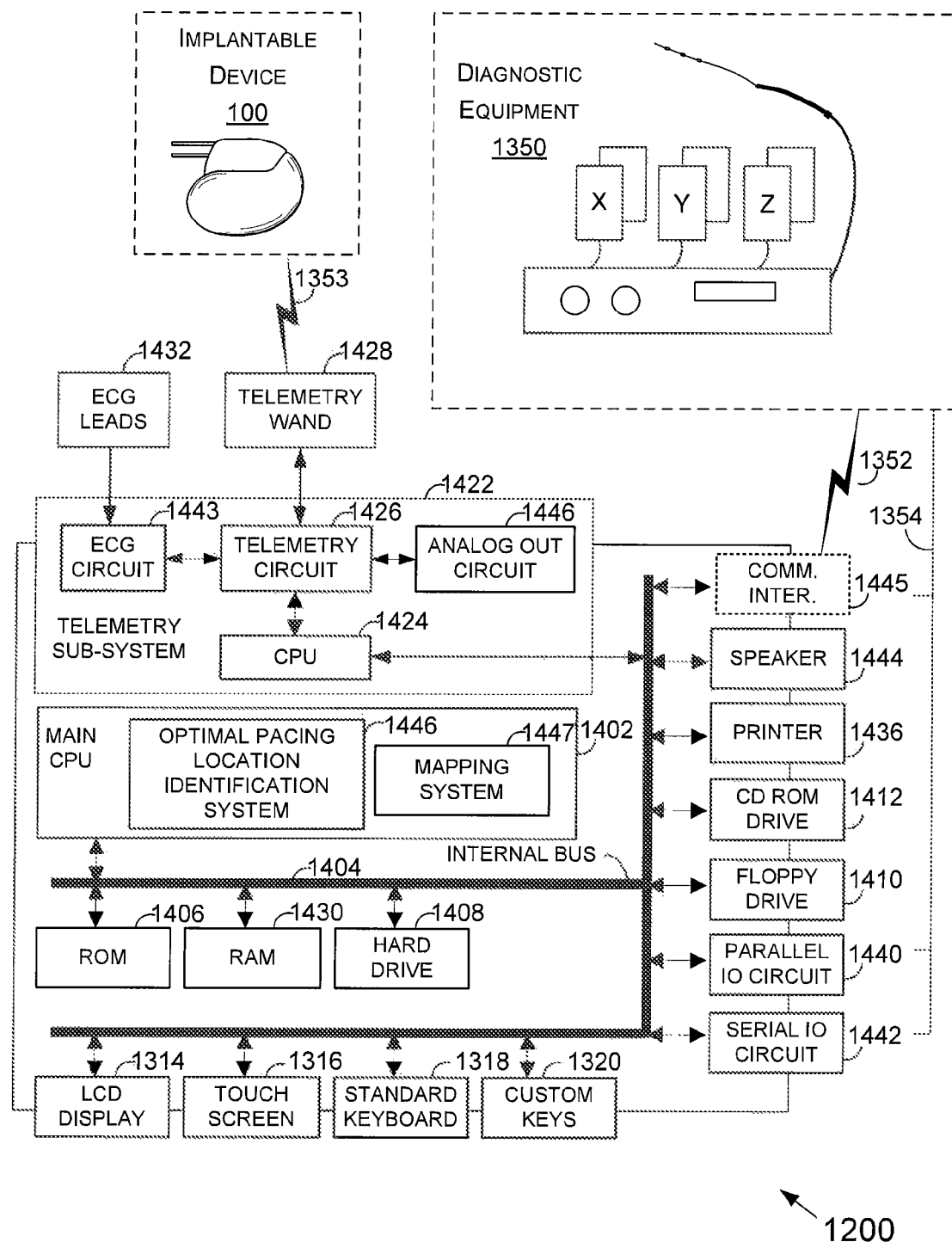
FIG. 12 is an exemplary system for acquiring information and analyzing information.

A computing device may be used to assess motion (see, e.g., the programmer 1200 of FIG. 12). Such a device may allow a user to step through cardiac motion information using a time increment. For example, motion contours may be generated for the time increment and overlaid on a diagram of the heart. In this example, the user may use a scroll bar or other suitable control to display motion contours for time increments during a cardiac cycle. This exemplary technique allows a clinician to visualize time and displacement information (i.e., motion information). When used in conjunction with delivery of stimulation energy, a clinician may use such a technique to optimize site or sites for delivery of stimulation energy (e.g., for an implantable CRT device).

An assessment may include generating contour plots of displacement of the myocardium based on potentials associated with two or more sites. An assessment may include assessing systolic cardiac motion at one or more sites and/or assessing diastolic cardiac motion at one or more sites. An assessment may generate motion data as displacement at a site versus time.

FIG. 11 shows an exemplary plot 1100 of data acquired during trials in an animal model. Data were acquired for a RA lead, an RV lead, a quadpolar lead in the anterior vein of the left ventricle, multipolar catheter in a lateral branch of the left ventricle and a basket catheter inserted endocardially in the left ventricle. The plot 110 shows extent of motion in a Cartesian coordinate system as well as general position of the various leads with respect to each other.

As described herein, an exemplary method can include positioning a pair of current-delivery electrodes in contact with a patient's body; advancing a multielectrode-bearing delivery device into the coronary sinus of the patient's heart and at least partially into a vein of the left ventricle; delivering current using the pair of current-delivery electrodes to generate a potential field; measuring potentials associated with the potential field using at least one electrode of the multielectrode-bearing delivery device; mapping motion of the multielectrode-bearing delivery device based on the measured potentials; advancing an electrode-bearing lead along the multielectrode-bearing delivery device; delivering current using the pair of current-delivery electrodes to generate a potential field; measuring potentials associated with the potential field using at least one electrode of the electrode-bearing lead; mapping motion of the electrode-bearing lead based on the measured potentials; determining the position of the electrode-bearing lead by comparing the mapped motion of the multielectrode-bearing delivery device and the mapped motion of the electrode-bearing lead; and after determining the position of the electrode-bearing lead, retracting the multielectrode-bearing delivery device while maintaining the position of the electrode-bearing lead. In such a method, the multielectrode-bearing delivery device may be a multifilar, electrode-bearing guidewire that includes, along its length, a successively fewer number of filars and where the multifilar, electrode-bearing guidewire has a varying flexibility along its length as a function of the successively fewer number of filars. Alternatively, the multielectrode-bearing delivery device may be a multielectrode catheter. The foregoing method can use a multielectrode-bearing delivery device to position a lead, optionally without X-ray based radiography.

As described herein, an exemplary system for positioning a multielectrode-bearing delivery device in a vein of the heart includes a multielectrode-bearing delivery device; an electrode-bearing lead positionable via the multielectrode-bearing delivery device; at least one pair of current-delivery electrodes to establish a coordinate system in a patient's body; and control logic to call for delivery of current to a pair of the current-delivery electrodes to generate a potential field, to call for measuring potentials associated with the potential field using at least one electrode of the multielectrode-bearing delivery device, to call for mapping motion of the at least one electrode of the multielectrode-bearing delivery device, to call for measuring potentials associated with the potential field using at least one electrode of the electrode-bearing lead, to call for mapping motion of the at least one electrode of the electrode-bearing lead, and to call for comparing mapped motion of at least one electrode of the multielectrode-bearing delivery device and at least one electrode of the electrode-bearing lead, and to output an indicator based at least in part on a comparison of mapped motion. In such a system, the indicator may be, for example, an audible indicator, a visual indicator, a tactile indicators or a combination of indicators. In the foregoing system, the multielectrode-bearing delivery device can be a multifilar, electrode-bearing guidewire that includes, along its length, a successively fewer number of filars and where the multifilar, electrode-bearing guidewire has a varying flexibility along its length as a function of the successively fewer number of filars. In an alternative, the multielectrode-bearing delivery device can be a multielectrode catheter.

Exemplary External Programmer

FIG. 12 illustrates pertinent components of an external programmer 1200 for use in programming an implantable medical device 100 (see, e.g., FIGS. 1 and 2). The external programmer 1200 optionally receives information from other diagnostic equipment 1350, which may be a computing device capable of acquiring motion information related to cardiac mechanics. For example, the equipment 1350 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1200 in distinguishing respiratory motion from cardiac motion.

Briefly, the programmer 1200 permits a clinician or other user to program the operation of the implanted device 100 and to retrieve and display information received from the implanted device 100 such as IEGM data and device diagnostic data. Where the device 100 includes a module such as the motion module 239, then the programmer 1200 may instruct the device 100 to measure potentials and to communicate measured potentials to the programmer via a communication link 1353. The programmer 1200 may also instruct a device or diagnostic equipment to deliver current to generate one or more potential fields within a patient's body where the implantable device 100 may be capable of measuring potentials associated with the field(s).

The external programmer 1200 may be configured to receive and displays ECG data from separate external ECG leads 1432 that may be attached to the patient. The programmer 1200 optionally receives ECG information from an ECG unit external to the programmer 1200. As already mentioned, the programmer 1200 may use techniques to account for respiratory motion.

Depending upon the specific programming of the external programmer 1200 may also be capable of processing and analyzing data received from the implanted device 100 and from ECG leads 1432 to, for example, render diagnosis as to medical conditions of the patient or to the operations of the implanted device 100. As noted, the programmer 1200 is also configured to receive data representative of conduction time delays from the atria to the ventricles and to determine, therefrom, an optimal or preferred location for pacing. Further, the programmer 1200 may receive information such as ECG information, IEGM information, information from diagnostic equipment, etc., and determine one or more stimulation sites.

Now, considering the components of programmer 1200, operations of the programmer are controlled by a CPU 1402, which may be a generally programmable microprocessor or microcontroller or may be a dedicated processing device such as an application specific integrated circuit (ASIC) or the like. Software instructions to be performed by the CPU are accessed via an internal bus 1404 from a read only memory (ROM) 1406 and random access memory 1430. Additional software may be accessed from a hard drive 1408, floppy drive 1410, and CD ROM drive 1412, or other suitable permanent or removable mass storage device. Depending upon the specific implementation, a basic input output system (BIOS) is retrieved from the ROM 1406 by CPU 1402 at power up. Based upon instructions provided in the BIOS, the CPU 1402 "boots up" the overall system in accordance with well-established computer processing techniques.

Once operating, the CPU 1402 displays a menu of programming options to the user via an LCD display 1314 or other suitable computer display device. To this end, the CPU 1402 may, for example, display a menu of specific programming parameters of the implanted device 100 to be programmed or may display a menu of types of diagnostic data to be retrieved and displayed. In response thereto, the clinician enters various commands via either a touch screen 1316 overlaid on the LCD display or through a standard keyboard 1318 supplemented by additional custom keys 1320, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to the determination of the optimal pacing location, CPU 1402 includes an optimal pacing location identification system 1446 and a 3-D mapping system 1447. The systems 1446 and 1447 may receive motion information from the implantable device 100 and/or diagnostic equipment 1350. The location identification system can optionally input data representative of time delays from the right atrium to the candidate locations in the ventricles, either from a sensing probe, the implanted device, or an EKG. The location identification system 1446 optionally includes control logic to associate information and to determine one or more stimulation sites. The location identification system may also include control logic to analyze information to aid in such a determination.

Where information is received from the implanted device 100, a telemetry wand 1428 may be used. Other forms of wireless communication exist as well as forms of communication where the body is used as a "wire" to communicate information from the implantable device 100 to the programmer 1200.

If information is received directly from diagnostic equipment 1350, any appropriate input may be used, such as parallel IO circuit 1440 or serial IO circuit 1442. Motion information received via the device 100 or via other diagnostic equipment 1350 may be analyzed using the mapping system 1447. In particular, the mapping system 1447 (e.g., control logic) may identify positions within the body of a patient and associate such positions with one or more electrodes where such electrodes may be capable of delivering stimulation energy to the heart.

A communication interface 1445 optionally allows for wired or wireless communication with diagnostic equipment 1350 or other equipment. The communication interface 1445 may be a network interface connected to a network (e.g., intranet, Internet, etc.).

A map or model of cardiac motion may be displayed using display 1214 based, in part, on 3-D heart information and optionally 3-D torso information that facilitates interpretation of motion information. Such 3-D information may be input via ports 1440, 1442, 1445 from, for example, a database, a 3-D imaging system, a 3-D location digitizing apparatus (e.g., stereotactic localization system with sensors and/or probes) capable of digitizing the 3-D location. According to such an example, a clinician can thereby view the optimal location for delivery of stimulation energy on a map of the heart to ensure that the location is acceptable before an electrode or electrodes are positioned and optionally fixed at that location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1200 optionally records procedures and allows for playback (e.g., for subsequent review). For example, a heart map and all of the motion data may be recorded for subsequent review, perhaps if an electrode needs to be repositioned. Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 1422 may include its own separate CPU 1424 for coordinating the operations of the telemetry subsystem. In a dual CPU system, the main CPU 1402 of programmer communicates with telemetry subsystem CPU 1424 via internal bus 1404. Telemetry subsystem additionally includes a telemetry circuit 1426 connected to telemetry wand 1428, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1200 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1200 (e.g., within a random access memory (RAM) 1430, hard drive 1408, within a floppy diskette placed within floppy drive 1410). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1200 has a communication link to an external storage device or network storage device, then information may be stored in such a manner (e.g., on-site database, off-site database, etc.). The programmer 1200 optionally receives data from such storage devices.

A typical procedure may include transferring all patient and device diagnostic data stored in an implanted device 100 to the programmer 1200. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 1322 receives ECG signals from ECG leads 1432 via an ECG processing circuit 1434. As with data retrieved from the implanted device 100, signals received from the ECG leads are stored within one or more of the storage devices of the programmer 1100. Typically, ECG leads output analog electrical signals representative of the ECG. Accordingly, ECG circuit 1434 includes analog to digital conversion circuitry for converting the signals to digital data appropriate for further processing within programmer 1200. Depending upon the implementation, the ECG circuit 1443 may be configured to convert the analog signals into event record data for ease of processing along with the event record data retrieved from the implanted device. Typically, signals received from the ECG leads 1432 are received and processed in real time.

Thus, the programmer 1200 is configured to receive data from a variety of sources such as, but not limited to, the implanted device 100, the diagnostic equipment 1350 and directly or indirectly via external ECG leads (e.g., subsystem 1422 or external ECG system). The diagnostic equipment 1350 includes wired 1354 and/or wireless capabilities 1352 which optionally operate via a network that includes the programmer 1200 and the diagnostic equipment 1350 or data storage associated with the diagnostic equipment 1350.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 1402, the programming commands are converted to specific programming parameters for transmission to the implanted device 100 via telemetry wand 1428 to thereby reprogram the implanted device 100 or other devices, as appropriate.

Prior to reprogramming specific parameters, the clinician may control the external programmer 1200 to display any or all of the data retrieved from the implanted device 100, from the ECG leads 1432, including displays of ECGs, IEGMs, statistical patient information (e.g., via a database or other source), diagnostic equipment 1350, etc. Any or all of the information displayed by programmer may also be printed using a printer 1436.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 1200 optionally includes a modem to permit direct transmission of data to other programmers via the public switched telephone network (PSTN) or other interconnection line, such as a T1 line or fiber optic cable. Depending upon the implementation, the modem may be connected directly to internal bus 1404 may be connected to the internal bus via either a parallel port 1440 or a serial port 1442.

Other peripheral devices may be connected to the external programmer via the parallel port 1440, the serial port 1442, the communication interface 1445, etc. Although one of each is shown, a plurality of input output (IO) ports might be provided. A speaker 1444 is included for providing audible tones to the user, such as a warning beep in the event improper input is provided by the clinician. Telemetry subsystem 1422 additionally includes an analog output circuit 1446 for controlling the transmission of analog output signals, such as IEGM signals output to an ECG machine or chart recorder.

With the programmer 1200 configured as shown, a clinician or other user operating the external programmer is capable of retrieving, processing and displaying a wide range of information received from the ECG leads 1432, from the implanted device 100, the diagnostic equipment 1350, etc., and to reprogram the implanted device 100 or other implanted devices if needed. The descriptions provided herein with respect to FIG. 12 are intended merely to provide an overview of the operation of programmer and are not intended to describe in detail every feature of the hardware and software of the device and is not intended to provide an exhaustive list of the functions performed by the device.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
  positioning a pair of current-delivery electrodes in contact with a patient's body;
  advancing a multielectrode-bearing delivery device into a coronary sinus and at least partially into a vein of a left ventricle of a patient's heart;
  positioning an electrode of the multielectrode-bearing device at an optimal location by: delivering current using the pair of current-delivery electrodes to generate a potential field; measuring potentials associated with the potential field using an electrode of the multielectrode-bearing delivery device; mapping motion of the electrode of the multielectrode-bearing delivery device based on the measured potential; and identifying an optimal electrode of the multielectrode-bearing device based on the mapped motion, wherein the location of the optimal electrode corresponds to the optimal location;
  positioning an electrode at the determined optimal location by: advancing an electrode-bearing lead along the multielectrode-bearing delivery device; and aligning an electrode of the electrode-bearing lead with the optimal electrode of the multielectrode-bearing delivery device;
  after aligning the electrode of the electrode-bearing lead, retracting the multielectrode-bearing delivery device while maintaining the position of the electrode-bearing lead.

2. The method of claim 1 wherein the determining the position of the electrode-bearing lead occurs without X-ray radiography.

3. The method of claim 1 wherein the multielectrode-bearing delivery device is a multifilar, electrode-bearing guidewire that comprises, along its length, a successively fewer number of filars and wherein the multifilar, electrode-bearing guidewire comprises a varying flexibility along its length as a function of the successively fewer number of filars.

4. The method of claim 1 wherein the multielectrode-bearing delivery device is a multielectrode catheter.

5. The method of claim 1 wherein positioning an electrode of the multielectrode-bearing device at an optimal location further comprises:
  moving the electrode of the multielectrode-bearing delivery device to at least one additional location;
  repeating the delivering, measuring and mapping; and
  comparing the mapped motions of the electrode of the multielectrode-bearing delivery device at the respective locations.

6. The method of claim 5 wherein the optimal location corresponds to the location at which the electrode of the multielectrode-bearing delivery device exhibits the greatest displacement.

7. The method of claim 1 wherein the multielectrode-bearing delivery device comprises a plurality of spaced apart electrodes and positioning an electrode of the multielectrode-bearing device at an optimal location comprises:
  measuring potentials associated with the potential field at a plurality of electrodes of the multielectrode-bearing delivery device;
  mapping motion of the plurality of the electrodes of the multielectrode-bearing delivery device based on the measured potential; and
  comparing the mapped motions of the plurality of electrodes of the multielectrode-bearing delivery device.

8. The method of claim 7 wherein the optimal location corresponds to the location of the electrode of the multielectrode-bearing delivery device that exhibits the greatest displacement.

9. The method of claim 1 wherein:
positioning an electrode of the multielectrode-bearing device at an optimal location further comprises delivering stimulation energy using the electrode of the multielectrode-bearing delivery device; and
mapping motion of the electrode of the multielectrode-bearing delivery device comprises mapping motion responsive to the stimulation energy.

10. The method of claim 1 wherein aligning an electrode of the electrode-bearing lead with the optimal electrode of the multielectrode-bearing delivery device comprises:
delivering current using the pair of current-delivery electrodes to generate a potential field;
measuring potentials associated with the potential field using the electrode of the electrode-bearing lead;
mapping motion of the electrode of the electrode-bearing lead based on the measured potentials; and
determining if the mapped motion of the electrode of the electrode-bearing lead tracks the mapped motion of the optimal electrode of the multielectrode-bearing delivery device.

11. The method of claim 10 wherein if the respective mapped motions do not track, aligning further comprises:
repositioning the electrode of the electrode-bearing device; and
repeating the delivering, measuring, mapping and repositioning to identify a position for the electrode of the electrode-bearing device that results in the greatest degree of tracking between the mapped motion of the electrode of the electrode-bearing lead and the mapped motion of the optimal electrode of the multielectrode-bearing delivery device.

12. The method of claim 10 wherein the electrode-bearing device comprises a plurality of spaced apart electrodes, and if the respective mapped motions do not track, aligning further comprises:
repeating the delivering, measuring, and mapping for a plurality of electrodes of the electrode-bearing device to identify the electrode of the electrode-bearing device having the greatest degree of tracking with the mapped motion of the optimal electrode of the multielectrode-bearing delivery device.

13. The method of claim 10 wherein determining if the mapped motion of the electrode of the electrode-bearing lead tracks the mapped motion of the electrode of the multielectrode-bearing delivery device comprises comparing position coordinates for the electrode of the electrode-bearing lead with position coordinates for the optimal electrode of the multielectrode-bearing delivery device.

14. The method of claim 13 wherein the position coordinates are Cartesian coordinates.

15. The method of claim 13 wherein the position coordinates are average position coordinates over a period of time.

16. The method of claim 1 wherein:
positioning an electrode of the electrode-bearing device at the optimal location further comprises delivering stimulation energy using the electrode of the electrode-bearing lead; and
mapping motion of the electrode of the electrode-bearing lead comprises mapping motion responsive to the stimulation energy.

17. The method of claim 1 wherein the multielectrode-bearing delivery device comprises a catheter with a lumen and advancing an electrode-bearing lead along the multielectrode-bearing delivery device comprises advancing the lead through the lumen.

18. The method of claim 1 wherein the multielectrode-bearing delivery device comprises a guidewire and advancing an electrode-bearing lead along the multielectrode-bearing delivery device comprises advancing the lead over the guidewire.

19. The method of claim 1 wherein the electrode-bearing lead is adapted for chronic implant.

* * * * *